(12) United States Patent
Drizen et al.

(10) Patent No.: US 6,251,436 B1
(45) Date of Patent: Jun. 26, 2001

(54) DRUG PREPARATIONS FOR TREATING SEXUAL DYSFUNCTION

(75) Inventors: Alan Drizen; Peter Rothbart, both of Ontario (CA); Gary M. Nath, Bethesda, MD (US)

(73) Assignee: L.A.M. Pharmaceutical Corporation, Miami, FL (US)

( * ) Notice: Subject to any disclaimer, the term of this patent is extended or adjusted under 35 U.S.C. 154(b) by 0 days.

(21) Appl. No.: 09/148,986

(22) Filed: Sep. 8, 1998

Related U.S. Application Data

(63) Continuation-in-part of application No. 09/048,335, filed on Mar. 26, 1998, now Pat. No. 6,036,977, which is a continuation-in-part of application No. 08/825,121, filed on Mar. 28, 1997, now Pat. No. 5,952,006, which is a continuation-in-part of application No. 08/796,578, filed on Feb. 6, 1997, now Pat. No. 5,897,880, which is a continuation-in-part of application No. 08/536,750, filed on Sep. 29, 1995, now abandoned.

(51) Int. Cl.$^7$ ............................ A61K 9/14; A61K 31/557
(52) U.S. Cl. ...................... 424/488; 424/484; 424/486; 514/54; 514/57; 514/530; 514/777; 514/781; 514/929; 514/944; 536/53
(58) Field of Search .................................. 424/486, 484, 424/488, 78.08, 777, 530, 781, 929; 514/54, 57, 944; 536/53

(56) References Cited

U.S. PATENT DOCUMENTS

| | | |
|---|---|---|
| 4,127,118 | 11/1978 | Latorre . |
| 4,521,421 | 6/1985 | Foreman . |
| 4,801,587 | 1/1989 | Voss et al. . |
| 5,015,474 | 5/1991 | Parnell . |
| 5,017,229 | 5/1991 | Burns et al. . |
| 5,059,603 | 10/1991 | Rubin . |
| 5,126,348 | 6/1992 | McMurray . |
| 5,143,724 | 9/1992 | Leshchiner et al. . |
| 5,190,962 | 3/1993 | Barberich et al. . |
| 5,190,967 | 3/1993 | Riley . |
| 5,256,652 | 10/1993 | El-Rashidy . |
| 5,278,192 | 1/1994 | Fung et al. . |
| 5,318,780 | 6/1994 | Viegas et al. . |
| 5,333,621 | 8/1994 | Denzer . |
| 5,380,757 | 1/1995 | Horrobin . |
| 5,380,758 | 1/1995 | Stamler et al. . |
| 5,399,581 | 3/1995 | Laragh . |
| 5,474,535 | 12/1995 | Place et al. . |
| 5,489,610 | 2/1996 | Fung et al. . |
| 5,525,357 | 6/1996 | Keefer et al. . |
| 5,527,893 | 6/1996 | Burns et al. . |
| 5,565,466 | 10/1996 | Gioco et al. . |
| 5,583,144 | 12/1996 | Kral . |
| 5,679,394 | 10/1997 | Long, Jr. et al. . |
| 5,731,339 | 3/1998 | Lowrey . |
| 5,741,511 | 4/1998 | Lee et al. . |
| 5,942,545 | * 8/1999 | Samour et al. ....................... 514/573 |
| 5,958,427 | * 9/1999 | Salzman et al. . |

FOREIGN PATENT DOCUMENTS

| | | |
|---|---|---|
| 0 266 968 | 10/1987 | (EP) . |
| 0 346 297 | 5/1989 | (EP) . |
| WO 93/0089 | 1/1993 | (WO) . |
| 9938472 | * 8/1999 | (WO) . |

OTHER PUBLICATIONS

Billmeyer. Textbook of Polymer Science. Interscience Publishers. New York, NY. 1962, see pp. 62–104.*
Kirk–Othmer. Encyclopedia of Chemical Technology, 2nd Ed. vol. 16, 1968, see pp. 242–253.*
Nakajima, "Fractionation of Linear Polyethylene with Gel Permeation Chromatography", Advances in Chemistry Series 125, Published by American Chemical Society, pp. 89–107 (1973).*
MUSE® (Alprostadil) (package insert), Vivu Inc. (1996).
Allen et al., "Objective Double–blind Evaluation of Erectile Function with Intracorporeal Papaverine in Combination with Phentolamine and/or Prostaglandin E1", *The Journal of Urology*, 148:1181–83 (1992).
Lakin et al., "Intracavernous Injection Therapy: Analysis of Results and Complications", *The Journal of Urology*, 143:1138–41 (1990).
Bennett et al., "An Improved Vasoactive Drug Combination for a Pharmacological Erection Program", *The Journal of Urology*, 146:1564–65 (1991).
Valdevenito et al., "Intracavernous Self–injection Pharmacotherapy Program: Analysis of Results and Complications", *Int. J. Impotence Res.*, 6:81–91 (1994).
Goldstein et al., "Oral Sildenafil in the Treatment of Erectile Dysfuction." *The New England Journal of Medicine*, vol. 338, No. 20:1397–1404 (1998).

* cited by examiner

Primary Examiner—Robert H. Harrison
(74) Attorney, Agent, or Firm—Nath & Associates PLLC; Gary M. Nath

(57) ABSTRACT

Topical gelled compositions comprising a drug which causes vasodilation, and optionally prostaglandin $E_1$, dispersed within a polymer matrix, and methods of treating sexual dysfunction, including both male and female sexual dysfunction, using said compositions.

12 Claims, No Drawings

DRUG PREPARATIONS FOR TREATING SEXUAL DYSFUNCTION

This application is a continuation-in-part of U.S. patent application Ser. No. 09/048,335 filed Mar. 26, 1998, U.S. Pat. No. 6,036,977, which is a continuation-in-part of U.S. patent application Ser. No. 08/825,121 filed Mar. 28, 1997, U.S. Pat. No. 5,952,006 which is a continuation-in-part of U.S. patent application Ser. No. 08/796,578 filed Feb. 6, 1997, U.S. Pat. No. 5,897,880 which is a continuation-in-part of U.S. patent application Ser. No. 08/536,750, filed Sep. 29, 1995 now abandoned the entire contents of which are hereby incorporated in their entirety.

FIELD OF THE INVENTION

This invention relates to the preparation of a transdermal delivery system. The preparation is designed to deliver therapeutic levels of a drug which causes vasodilation, and optionally prostaglandin $E_1$, to specific sites below the dermal level of the skin. Specifically, the preparations address sexual dysfunction caused by impotency in males and vaginal dryness in females.

DESCRIPTION OF THE PRIOR ART

Over the years, methods have been developed to achieve the efficient delivery of a therapeutic drug to a mammalian body part requiring pharmaceutical treatment. Use of an aqueous liquid which can be applied at room temperature as a liquid but which forms a semi-solid gel when warmed to body temperature has been utilized as a vehicle for some drug delivery since such a system combines ease of application with greater retention at the site requiring treatment than would be the case if the aqueous composition were not converted to a gel as it is warmed to mammalian body temperature. In U.S. Pat. No. 4,188,373, PLURONIC® polyols are used in aqueous compositions to provide thermally gelling aqueous systems. Adjusting the concentration of the polymer provides the desired sol-gel transition temperature, that is, the lower the concentration of polymer, the higher the sol-gel transition temperature, after crossing a critical concentration minimum, below which a gel will not form.

In U.S. Pat. Nos. 4,474,751 and 4,478,822, drug delivery systems are described which utilize thermosetting gels; the unique feature of these systems is that both the gel transition temperature and/or the rigidity of the gel can be modified by adjusting the pH and/or the ionic strength, as well as by the concentration of the polymer.

Other patents disclosing pharmaceutical compositions which rely upon an aqueous gel composition as a vehicle for the application of the drug are U.S. Pat. Nos. 4,883,660; 4,767,619; 4,511,563; 4,861,760; and 5,318,780. Thermosetting gel systems are also disclosed for application to injured mammalian tissues of the thoracic or peritoneal cavities in U.S. Pat. No. 4,911,926.

Ionic polysaccharides have been used in the application of drugs by controlled release. Such ionic polysaccharides as chitosan or sodium alginate are disclosed as useful in providing spherical agglomerates of water-insoluble drugs in the Journal of Pharmaceutical Sciences, Volume 78, Number 11, November 1989, Bodmeier et al. Calcium alginate gel formulations have also found use as a matrix material for the controlled release of herbicides, as disclosed in the Journal of Controlled Release, (1986), pages 229–233, Pfizer et al.

In U.S. Pat. No. 3,640,741, a molded plastic mass composed of the reaction product of a hydrophilic colloid and a cross-linking agent such as a liquid polyol, also containing an organic liquid medium such as glycerin, is disclosed as useful in the controlled release of medication or other additives. The hydrophilic colloid can be carboxymethyl cellulose gum or a natural alginate gum which is cross-linked with a polyol. The cross-linking reaction is accelerated in the presence of aluminum and calcium salts.

In U.S. Pat. No. 4,895,724, compositions are disclosed for the controlled release of pharmacological macromolecular compounds contained in a matrix of chitosan. Chitosan can be cross-linked utilizing aldehydes, epichlorohydrin and benzoquinone.

In U.S. Pat. No. 4,795,642, there are disclosed gelatin-encapsulated, controlled-release compositions for release of pharmaceutical compositions, wherein the gelatin encloses a solid matrix formed by the cation-assisted gelation of a liquid filling composition incorporating a vegetable gum together with a pharmaceutically-active compound. The vegetable gums are disclosed as polysaccharide gums such as alginates which can be gelled utilizing a cationic gelling agent such as an alkaline earth metal cation.

While the prior art is silent with respect to aqueous drug delivery vehicles and isotonicity thereof, osmotic drug delivery systems are disclosed in U.S. Pat. No. 4,439,196 which utilize a multi-chamber compartment for holding osmotic agents, adjuvants, enzymes, drugs, pro-drugs, pesticides, and the like. These materials are enclosed by semipermeable membranes so as to allow the fluids within the chambers to diffuse into the environment into which the osmotic drug delivery system is in contact. The drug delivery device can be sized for oral ingestion, implantation, rectal, vaginal, or ocular insertion for delivery of a drug or other beneficial substance. Since this drug delivery device relies on the permeability of the semipermeable membranes to control the rate of delivery of the drug, the drugs or other pharmaceutical preparations by definition, are not isotonic with mammalian blood.

Finding a suitable drug delivery vehicle for the treatment of erectile dysfunction has proven to be particularly difficult. Male erectile dysfunction, the persistent inability of a man to achieve or maintain an erection sufficient for satisfactory sexual performance, is estimated to affect up to 30 million men in the United States. See "Oral Sildenafil in the Treatment of Erectile Dysfunction", *New England Journal of Medicine*, 338:20:1397 (1998). There are numerous causes of male erectile dysfunction. For example, it may be atonic, due to paralysis of the motor nerves without any evidence of lesions to the central nervous system, particularly the spinal cord. Alternatively, it could be psychic, and dependent on a mental problem or instability. Finally, it could be symptomatic, due to some other disorder, such as injury to nerves in the perineal region, by virtue of which the sensory portion of the erection reflex is blocked out.

Various available treatments have been employed in the treatment of male erectile dysfunction, including vacuum-constriction devices, intracavernosal injections of vasoactive agents, transurethral delivery of prostaglandin $E_1$ (alprostadil), oral administration of sildenafil citrate (Viagra® available from Pfizer), implantation of penile prostheses, and venous or arterial surgery. Most of these treatments involve painful procedures with varying degrees of success that are often associated with numerous side effects. Moreover, many persons are not candidates for one or more of these treatments as a result of their physiological condition. For example, oral admistration of sildenafil citrate is contraindicated for individuals currently taking organic nitrates, such a nitroglycerine. See "VIAGRA® (sildenafil citrate) Tablets", Pfizer Labs, 7 (1998).

The medications most commonly used to treat male erectile dysfunction have been papaverine hydrochloride, a smooth muscle relaxant, phentolamine mesylate, an α-adrenergic blocker, and several other drugs which are used because of their ability to cause vasodilation. Recent data have suggested that prostaglandin $E_1$ either alone or in combination with papaverine produces an improved erectile response. The use of these drugs often requires special applicators, which besides being cumbersome, are also painful to use. However, the use of topical gels, creams and ointments for treating impotency has been proposed in several publications.

U.S. Pat. No. 5,583,144 discloses compositions for relieving erectile impotence in men which contain piperoxan in a pharmaceutically acceptable carrier. As the pharmaceutically acceptable carrier, commercially available gels, ointment and creams, such as the hydrogel, hydroxypropylmethylcellulose are optionally used. The patent does not address the importance of the rate of delivery to the site of action.

U.S. Pat. No. 5,256,652 discloses a topical composition which enhances the maintenance of penis erection and which contains a peripheral vasodilator, an absorption enhancer and, optionally, a vasocontrictor and an alpha receptor combined with a pharmacologically acceptable topical vehicle. The patent discloses that "[t]he problem with topically administered drugs is their limited penetration of the drug through the skin" and encourages the use of a skin penetration enhancer. See column 2, lines 59–65. There is no teaching or warning that the rate or amount of absorption may be too high to be effective as the result of drug entering fatty tissue.

U.S. Pat. No. 5,059,603 discloses topical compositions for treating impotence which contain a vasodilator, a vasoconstrictor and an absorption enhancing agent in a pharmaceutically acceptable carrier. The patent also teaches that nicotinyl alcohol may be used as the vasodilator, but that side effects such as flushing and gastrointestinal disturbances may result.

U.S. Pat. No. 4,801,587 discloses a vasodilator or alpha-blocker in an ointment base. However, the patent teaches that a drug carrier is only optionally used when necessary to increase absorption. The patent urges the importance of increasing absorption into the skin while not addressing the proper rate of absorption necessary to attain therapeutically effective amounts at the site of action.

To date there has been little objective data comparing the relative efficacy of the above described medications either alone or in combination. Further, the delivery systems disclosed in the above references have lacked the sophistication necessary to deliver the drug at a rate which provides a therapeutically effective amount at the active site when needed and for an appropriate amount of time. Moreover, the disclosed topical formulations are generally not storage stable.

It is also important to note that sexual dysfunction is not limited to men. Many women, particularly menopausal women, women suffering from an autoimmune disease and women undergoing radiation therapy, experience vaginal dryness caused by loss of normal vulval and vaginal secretions, particularly during sexual activity, resulting in difficulty with or an inability to achieve intercourse. Currently, there are only a limited number of available therapies which address the problem of vaginal dryness. Though in mild cases, local hygiene and antipruritic ointments and creams may be beneficial, typically additional therapy will be necessary. Some currently available therapies involve treatment with hormone-based formulas containing either testosterone or glucocorticoids. Parnell, U.S. Pat. No. 5,380,757, discloses a therapy involving treatments with gamma-linolenic acid (GLA) and dihomo-gamma-linolenic acid (DGLA). U.S. Pat. No. 4,347,237 discloses a vaginal suppository composed of a variety of different types of water soluble polyoxy alkylene polyol components.

However, the formulations disclosed in the prior art are all deficient in that the delivery systems which they employ do not carefully control the rate of delivery of the active therapeutic agent which in turn can lead to adverse effects. For example, currently used testosterone treatments can produce clitoral enlargement or other masculinization, and glucocorticoids when used for long periods of time carry a serious risk of producing atrophy and thinning of the epithelium.

A need thus exists for therapeutic compositions for treating sexual dysfunction in men and women that are applied topically and transported through the skin, or administered by injection, without concomitant presence of pain, side effects, high risk of infection, inconvenience or interference with the spontaneity of the sex act and with a highly efficacious result, and methods for using same. Moreover, a need exists for a treatment for erectile dysfunction that may be used in conjunction with cardiovascular agents, such as organic nitrates.

SUMMARY OF THE INVENTION

The present invention relates to the formation of gelled compositions and methods for using said gelled compositions in treating sexual dysfunction, including impotency or erectile dysfunction in males, and sexual dysfunction in females caused by vaginal dryness. The methods of the invention comprise topically applying to a specific site on the surface of an animal a therapeutically effective amount of a drug which causes vasodilation dispersed within a gelled composition comprising a polymer matrix which is suspended in a liquid medium, wherein the polymer matrix contains a negative charged polymer blended with a nonionic polymer, and wherein the molar ratio of the negative charged polymer to the nonionic polymer is 1:4 to 0.09, and the negative charged polymer is present in amounts of about 1.0% to about 3.5% by weight.

In a preferred embodiment of the invention, the gelled composition contains prostaglandin $E_1$, in addition to the drug which causes vasodilation.

In a further preferred embodiment of the invention, a method for the treatment of erectile dysfunction in a male animal comprises topically applying to the surface of a penis a therapeutically effective amount of a drug which causes vasodilation, and optionally prostaglandin $E_1$, dispersed within a gelled composition comprising a polymer matrix which is suspended in a liquid medium; wherein the polymer matrix contains a negative charged polymer blended with a nonionic polymer; and wherein the molar ratio of the negative charged polymer to the nonionic polymer is 1:0.5 to 0.09 and the negative charged polymer is present in amounts of about 2.0% to about 3.5% by weight.

In another preferred embodiment of the invention, a gelled composition for treating impotency comprises therapeutically effective amounts of a drug which causes vasodilation, and optionally prostaglandin $E_1$, dispersed within a matrix containing a negative charged polymer blended with a nonionic polymer, wherein the molar ratio of the negative charged polymer to the nonionic polymer is 1:4 to 0.09 and the negative charged polymer is present in amounts of about 1.0% to about 3.5% by weight.

In yet another embodiment of the invention, a method for the treatment of erectile dysfunction in male animals comprises injecting into the corpora cavernosa a therapeutically effective amount of a drug which causes vasodilation, and optionally prostaglandin $E_1$, dispersed within a gelled composition comprising a polymer matrix which is suspended in a liquid medium; wherein the polymer matrix contains a negative charged polymer blended with a nonionic polymer; and wherein the molar ratio of the negative charged polymer to the nonionic polymer is 1:4 to 0.09 and the negative charged polymer is present in amounts of about 1.0 to about 3.5% by weight.

In a further embodiment of the invention, a method for the treatment of sexual dysfunction or vaginal dryness in a female animal comprises topically applying to the surface of a vagina a therapeutically effective amount of a drug which causes vasodilation, and optionally prostaglandin $E_1$, dispersed within a gelled composition comprising a polymer matrix which is suspended in a liquid medium, and wherein the polymer matrix contains a negatively charged polymer blended with a nonionic polymer, and wherein the molar ratio of the negative charged polymer to the nonionic polymer is 1:4 to 0.09 and the negative charged polymer is present in amounts of about 1.0% to about 3.5% by weight.

In a still further embodiment of the invention, a gelled composition for treating vaginal dryness comprises therapeutically effective amounts of a drug which causes vasodilation, and optionally prostaglandin $E_1$, dispersed within a matrix containing a negative charged polymer having a mean average molecular weight between about 650,000 and 800,000 blended with a nonionic polymer, wherein the molar ratio of the negative charged polymer to the nonionic polymer is 1:4 to 0.09 and the negative charged polymer is present in amounts of about 1.0% to about 3.5% by weight.

DETAILED DESCRIPTION OF THE INVENTION

It has been unexpectedly discovered that an effective therapeutic level of a drug may be administered topically and transdermally delivered through the skin into various sites where the drug is therapeutically effective. In order for this to be accomplished, it has been discovered that the active drug must be suspended or entrapped in a specially designed polymer matrix containing a specific molar ratio of negatively charged polymers and a non-ionic polymer suspended or dissolved in water and solubilizers.

This system is believed to form a matrix which microencapsulates, suspends, and/or entraps the active drug entity such that when it is administered, it is slowly released into the systemic circulatory system or muscular tissue providing a method of delivering an active drug to an affected site in the body through the skin.

The molar ratio of the polymers present in the matrix is critical in this invention. It has been found that molar ratios of the negative charged polymer to the non-ionic polymer must be from 1:4 to 0.09, and preferably from 1:2.5 to 0.1, and most preferably from 1:0.4 to 0.2. For transdermal delivery of drugs, it has been found that ratios either higher or lower than these levels will result in a polymer shearing effect which produces unacceptable turbulence and air pockets in the composition with resulting loss of potency and efficacy. Furthermore, the solutions tend to separate and form distinct polymer layers when ionic molarity is not appropriate. While gels and other topical therapeutic compositions generally encounter problems with storage stability, the present invention demonstrates an unexpectedly superior storage stability.

At least one of the polymers used to form the matrix of this invention must be sufficiently negatively charged to aid in the dispersion, encapsulation or solubilization of the drug. The viscosity and molecular weight of the negative charged polymer is also critical to the invention. Further, at least one of the polymers of the invention must be a nonionic polymer. The viscosity and molecular weight of the nonionic polymer is also critical to the invention. Particularly preferred nonionic polymers which have a viscosity of about 1,500 for a 5% solution to about 5,500 for a 1% solution have been found to be suitable for forming a polymer matrix capable of transdermal drug delivery. For drug delivery, using nonionic polymers with viscosities below these ranges will result in an excessive rate of release leading to drug dispersion into fatty tissue, causing reduced efficacy, while requiring higher levels of drug with accompanying side effects. Using nonionic polymers with a viscosity above these ranges will result in solid materials which are unsuitable for transdermal drug delivery.

As discussed herein, viscosity, or solution viscosity, refers to the intrinsic viscosity of a polymer in solution (the viscosity which the unassociated polymer molecules give to the solution) and is a function of the molecular weight and very easily measured. Intrinsic viscosity is commonly used for control purposes, and the values can be converted into molecular weight by calibration with osmotic pressure, light scattering, or sedimentation measurements. The viscosity measurements and ranges used herein were provided by Aqualon, a division of Hercules, Inc., in its product specifications for Natrosol® (hydroxyethyl-cellulose), and all were Brookfield viscosities measured at 25° C. It is well within the capabilities of an ordinarily skilled artisan to obtain and/or identify polymers within the ranges specified by the invention.

Particularly preferred negative charged polymers which have mean average molecular weights below about 800,000 and preferably molecular weights between 650,000 to 800,000 have been found acceptable to form usable polymer matrixes for transdermal delivery. Polymers with average molecular weights between 700,000 and 775,000 are most preferred. Polymers having molecular weights above about 800,000 form solid gels in solution and are unable to serve as part of a transdermal delivery system. Furthermore, the polymers must be sterilizable and be stable during sterilization so that the polymer does not lose molecular weight once formulated into the final transdermal delivery form.

Exemplary, non-limiting examples of compounds that may be used as a source of this molecular weight polymer include polysulfated glucosoglycans, glucosaminoglycans, and mucopolysaccharides, derivatives thereof and mixtures thereof. Particularly preferred mucopolysaccharides are chondroitin sulfate and hyaluronic acid salts. Exemplary hyaluronate salts include sodium, calcium, potassium and magnesium salts with hyaluronate sodium being most preferred.

Hyaluronic acid (NAHA) occurs naturally in joint synovial fluid, where it plays a lubricating role, and may have biological activity as well. NAHA is a mucopolysaccharide, and may alternatively be referred to as glucosaminoglycan. The repeating unit of the hyaluronic acid molecule is a disaccharide consisting of D-glucuronic acid and N-acetyl-D-glucosamine. Because hyaluronic acid possesses a negative charge at neutral pH, it is soluble in water, where it forms highly viscous solutions. The D-glucuronic acid unit and N-acetyl-D-glucosamine unit are bonded through a glycosidic, beta (1-3) linkage, while each disaccharide unit is bonded to the next disaccharide unit through a beta (1-5) linkage. The (beta 1-4) linkages may be broken through hydrolysis with the enzyme hyaluronidase.

A variety of substances, commonly referred to as hyaluronic acid, have been isolated by numerous methods from various tissue sources including umbilical cords, skin, vitreous humor, synovial fluid, tumors, hemolytic streptocci pigskin, rooster combs, and the walls of veins and arteries. It is also being synthesized artificially and by recombinant technology.

Conventional methods for obtaining hyaluronic acid results with a product having differing properties and a wide range of viscosities. U.S. Pat. No. 2,585,546 to Hadian, discloses an example of a method for obtaining hyaluronic acid and which involves extracting acetone-washed umbilical cords with a dilute salt solution, acidifying the resulting extract, removing the clot so formed, precipitating some hyaluronic acid with protein from the acidified extract with ammonium sulfate, agitating the liquid with pyridine, precipitating another fraction highly contaminated with protein, followed by more ammonium sulfate which forces some pyridine out of solution along with the high viscosity hyaluronic acid. The hyaluronic acid collects at the interface between the two liquid phases and may be separated by filtration, centrifugation or another usual procedure. A modification of this process involves the fractionation of the acidic salt extract from umbilical cords with alcohol and ammonium sulfate. Alcohol is added to the acidic salt extract, and the resulting precipitate is removed. Solid ammonium sulfate is added to the liquid until saturation and the solution forms two phases with a precipitate of hyaluronic acid at the interface.

U.S. Pat. No. 4,517,296 is directed to the preparation of hyaluronic acid in high yield from Streptococcus bacteria by fermenting the bacteria under anaerobic conditions in a $CO_2$ enriched growth medium, separating the bacteria from the resulting broth and isolating the hyaluronic acid from the remaining constituents of the broth. Separation of the microorganisms from the hyaluronic acid is facilitated by killing the bacteria with trichloroacetic acid. After removal of the bacteria cells and concentration of the higher molecular weight fermentation products, the hyaluronic acid is isolated and purified by precipitation, resuspension and reprecipitation.

One particular fraction of hyaluronic acid (HA) that exhibits excellent matrix formation according to the present invention is hyaluronate sodium having a mean or average molecular weight between 650,000–800,000, preferably 700,000–775,000 with a high degree of purity, 95–105% free, and preferably at least 98% pure, from contamination of related mucopolysaccharides. Furthermore, this hyaluronic acid has a sulphated ash content of less than 15% and a protein content of less than 5%. Examples of usable base salts include those safe from animal and human use, such as sodium, potassium, calcium, and magnesium salts or the like.

In contrast to HA, chondroitins are mucopolysaccharides comprising repeating units of D-glucuronic acid and N-acetyl-D-galactosamine. Chondroitin sulphates are important components of cartilage and bone and are excellent for preparing the polymer matrix herein.

The negative charged polymers are generally present in the system in amounts which enable a semi-solid gel to be formed. Generally, gels are formed using amounts of about 1.0 to about 3.5% by weight with amounts of about 2.1 to about 2.5% by weight being preferred for use as a topical gel. Concentrations of negative charged polymer greater than 3.5% result in solids which are not suitable for pharmaceutical use.

The solutions used to prepare the gels of the present invention may be prepared in a variety of ways. For example, the polymers may be dissolved in water and purified either separately or jointly and then the optional active drug added to the system.

A particularly preferred procedure involves separately dissolving the nonionic polymer in water and centrifuging the material to form a solution and remove impurities. This may be conveniently done at rotation speeds of 2000 rpm for times of about 30 minutes to about two hours.

In contrast, the negative charged polymer may be blended and stirred in water until it is dissolved. This process must be done while avoiding the formation of bubbles and while freeing the polymer of its electrostatic activity. Furthermore, the molecular weight of the polymer must not be significantly changed during processing and as such mild process conditions are required. Processing conditions of 400–3000 rpm for durations of 16–24 hours have been found acceptable to produce stable solutions or gels of the charged polymer.

Conventional pharmaceutically acceptable emulsifiers, suspending agents, antioxidants (such as sodium metabisulfate) and preservatives (such as benzyl alcohol) may then be added to this system. Once all the components are blended together, such as by mixing 400–3000 rpm for one to four hours, the system is filled into tubes and sterilized. The resulting system is a clear gel which is storage stable for several years.

The drug may be added to the homogenous solution or gel separately once dissolved or disbursed in water. Emulsifiers, suspending agents and preservatives may then be added to this system. One particularly nonlimiting effective material for solubilizing water insoluble drugs is methoxypolyethylene glycol (MPEG). Once all the components are blended together, for 400–3000 rpm for 1 to 4 hours, the system is filled into tubes and sterilized. The resulting system is storage stable for several years.

The formulations may be used topically and also contain conventional pharmaceutically acceptable excipients well known to those skilled in the art, such as surfactants, suspending agents, emulsifiers osmotic enhancers, extenders and dilutants, pH modifiers as well as fragrances, colors, flavors and other additives.

As used herein, "genital area" refers to the general area of a male or female which contains or surrounds the genital organs. The compositions may be directly applied anywhere on the epidermis of the genital area. For highest efficacy in males, the composition should be applied to the epidermis of the penis and testicles. For highest efficacy in females, the composition should be applied directly to the vagina.

As indicated above, the active drug agents may be blended with the aqueous polymer matrix at the time of manufacture. As such, the drug when in the form of a water-soluble solid is simply diluted with sterilized water or polymer matrix solution and prepared in gel form.

The dosage system can be formed with or without the use of pharmaceutically acceptable preservatives. A significant advantage of the dosage form of the present system relates to its ability to allow the drug to slowly diffuse through tissue when administered thus allowing for an effective therapeutic dose to be present for long periods of time, i.e., 15 minutes to several hours.

In this regard, it should be noted that reference to therapeutically effective dose does not necessarily relate to conventional dosage levels, but does relate to drug levels that achieve an effective therapeutic level at the dose employed, which may be the same level but not at the same frequency of administration previously required for drugs taken orally or by injection. This not only significantly reduces the number of doses required to achieve the same effect, but it also reduces costs, maintenance and health hazards associated with conventional treatment therapies.

Doses may vary from patient to patient depending on the type and severity of the condition being treated and the drug being administered. Generally, doses of 150 mcg to 1000 mcg may be administered with preferred doses using 200 to 500 mcg of drug disbursed in the gelled matrix system. The total dosage of the gelled matrix with drug is usually 0.5 ml to 5 ml in volume. When the drug which causes vasodilation is niacin, it preferably will range from about 1% to about 15% by weight of the total composition. More preferably, the amount of niacin in the total composition will range from about 2% to about 12% by weight. Most preferably, the amount of niacin in the total composition will range from about 3% to about 6% by weight. The preferred amount of total composition in each dose will range between about 1 ml and 3 ml. in volume.

There is a physiological basis for the treatment of both male and female sexual dysfunctions together since they have physiological responses in common. See Foreman, U.S. Pat. No. 4,521,421. With regard to male sexual dysfunction, it is generally recognized that primary erectile dysfunction is almost always due to intraphsychic factors. In rare cases, biogenic factors, usually associated with low testosterone levels and reflecting disorders of the hypothalamic-pituitary-gonadal axis, provide the major etiology. Occasionally, vascular abnormalities are found. Physical factors include systemic diseases (e.g., diabetes mellitus [the most common], syphilis, alcoholism, drug dependency, hypopituitarism, and hypothyroidism); local disorders (e.g., congenital abnormalities and inflammatory diseases of the genitalia); vascular disturbances such as aortic aneurysm and atherosclerosis (e.g., Leriche's syndrome); neurogenic disorders (e.g., multiple sclerosis, spinal cord lesions, pituitary mifcroadenoma with hyperprolactinemia, and cardiovascular accident); drugs such as hypertensives, sedatives, tranquilizers, and amphetamines; and surgical procedures such as sympathectomy, prostatectomy and castration produce varying effects. Impotence is usually not induced by transurethral prostatectomy, whereas it almost always occurs after perineal prostatectomy. However, retrograde ejaculation is produced in the vast majority of men, irrespective of the type of prostatectomy.

Pharmacological erection therapy is an effective method to treat male erectile dysfunction. The medications most commonly used have been papaverine hydrochloride, a smooth muscle relaxant, and phentolamine mesylate, an α-adrenergic blocker. Recent data have suggested that prostaglandin $E_1$ either alone or in combination with papaverine produces an improved erectile response.

There currently is increasing evidence that prostaglandin $E_1$ is presently the single most effective agent for pharmacological erection therapy. The present invention contemplates using prostaglandin $E_1$ as a catalyst to be used in conjunction with a drug which causes vasodilation in cases in which the drug which causes vasodilation may not alone be effective. The combination of a drug which causes vasodilation and prostaglandin $E_1$ in conjunction with the claimed drug delivery system of the present invention provides a highly potent and efficacious therapeutic substance which may induce a response in subjects for whom all other available therapies are ineffective and without side effects or pain. Prostaglandin $E_1$ is a physiological agent that is metabolized locally within the cavernous tissue and there appears to be a low incidence of corporeal fibrosis, priapism or systemic reactions associated with its use. Several studies using subjective evaluation have shown that prostaglandin $E_1$ is more effective than a combination of papaverine and phentolamine. Lee et al. found that two-thirds of the men who failed prior intracavernous therapy with papaverine and phentolamine achieved adequate erections with prostaglandin $E_1$. Prostaglandin $E_1$ has also been found to be extremely effective as a single agent in several other studies. Liu et al. recently reported that prostaglandin $E_1$ is at least as effective as papaverine in increasing penile blood flow measured by duplex sonography. Prostaglandin $E_1$ has the advantage over papaverine of a slower onset, longer maintenance and less chance of priapism. Despite these advantages, however, prostaglandin $E_1$ is associated with a significant incidence of penile discomfort.

Prostaglandin $E_1$ is a naturally occurring acidic lipid that is synthesized from fatty acid precursors by most mammalian tissues and has a variety of pharmacologic effects. Human seminal fluid is a rich source of prostaglandins, including $PGE_1$ and $PGE_2$, and the total concentration of prostaglandins in ejaculate has been estimated to be approximately 100–200 mcg/mL. In vitro, alprostadil ($PGE_1$) has been shown to cause dose-dependent smooth muscle relaxation in isolated corpus cavernosum and corpus spongiosum preparations. Additionally, vasodilation has been demonstrated in isolated cavernosal artery segments that were pre-contracted with either norepinephrine or prostaglandin $E_{2\alpha}$. The vasodilatory effects of alprostadil on the cavernosal arteries and the trabecular smooth muscle of the corpora cavernosa result in rapid arterial inflow and expansion of the lacunar spaces within the corpora. As the expanded corporal sinusoids are compressed against the tunica albuginea, venous outflow through subtunical vessels is impeded and penile rigidity develops. This process is referred to as the corporal veno-occlusive mechanism.

The most notable systemic effects of alprostadil are vasodilation, inhibition of platelet aggregation, and stimulation of intestinal and uterine smooth muscle. Intravenous doses of 1 to 10 micrograms per kilogram of body weight lower blood pressure in mammals by decreasing peripheral resistance. Reflex increases in cardiac output and heart rate may accompany these effects.

Alprostadil is rapidly metabolized locally by enzymatic oxidation of the 15-hydroxyl group to 15-keto-$PGE_1$. The enzyme catalyzing this process has been isolated from many tissues in the lower genitourinary tract including the urethra, prostate, and corpus cavernosum. 15-keto-$PGE_1$ retains little (1–2%) of the biological activity of $PGE_1$. 15-keto-$PGE_1$ is rapidly reduced at the $C_{13}$–$C_{14}$ position to form the most abundant metabolite in plasma, 13,14-dihydro,15-keto $PGE_1$ (DKH-$PGE_1$), which is biologically inactive. The majority of DKH-$PGE_1$ is further metabolized to smaller prostaglandin remnants that are cleared primarily by the kidney and liver. Between 60% and 90% of $PGE_1$ has been shown to be metabolized after one pass through the pulmonary capillary beds. Use of the present formulations either alone or in combination with various therapeutic agents overcomes all of these prior art deficiencies.

The drug which causes vasodilation may be any pharmaceutically acceptable substance which causes any vasodilation either directly or indirectly when administered to an animal. In particular, the drug which causes vasodilation may be any drug which is classified, without limitation, in one of the following categories: vasodilators, nitrovasodilators, ACE inhibitors, angiotensin receptor antagonists, phosphodiesterase inhibitors, direct vasodilators, adrenergic receptor antagonists, calcium channel blocking drugs, alpha blockers, beta blockers, lympathomimetics, vitamins, organic nitrates, serotonin receptor blocking agents, angina blocking agents, other anti-hypertensive agents, cardiac stimulating agents, agents which improve renal vascular function, sympathomimetic amine and mixtures thereof.

Particularly preferred drugs which cause vasodilation include, without limitation, any of the following: niacin, nitroglycerine, nilatrin hydrochloride, pentoxyphylene, phenoxybenzamine, dichlophenac, papaverine, hydralazine, hydrazaline, hydrochloride, hydrochlorothiazide, sodiumnitroprusside, isoxaprine hydrochloride, epoprostenol sodium, nylidrin hydrochloride, tolazoline hydrochloride, nicotinyl alcohol, phentolamine, phentolamine mesylate, pentolamine hydrochloride, yohimbine, thymoxamine imipramine, verapamil, isoxsuprine, naftidrofuryl, tolazoline, hydroisosorbide, dibenamine, dinitrate, captopril, enalapril, enalaprilat, quinapril, lisinopril, ramipril, losartan, amrinone, milrinone, vesnarinone, nicorandil, prazosin, labetalol, celiprolol, carvedilol, bucindolol, nifedipine dobutamine, minoxidil, nylidrin, and salts thereof, derivatives thereof, precursors thereof and mixtures thereof.

Most preferably, the drug which causes vasodilation is selected from the group consisting of niacin, nicotinic acid, nicotinic acid precursors, esters of nicotinic acid and mixtures thereof.

Regardless of the route of administration elected, the formulations of the present invention are formulated into pharmaceutically acceptable dosage forms by conventional methods known in the pharmaceutical art.

As discussed above, an effective but nontoxic amount of the system is employed in treatment. The dose regimen for administering drugs or treating various conditions, such as pain as described above, is selected in accordance with a variety of factors including the type, age, weight, sex, and medical condition of the subject, the severity of the pain, the route of administration and the particular complex or combination of drugs employed. Determination of the proper dose for a particular situation is within the skill of the art. Generally, treatment is initiated with smaller dosages which are less than the optimum doses of the compound. Thereafter, the dose is increased by small increments until the optimum effect under the circumstances is reached. For convenience, the total daily dosage may be divided and administered in portions during the day if desired. Generally, amounts of drug may vary from 0.0001% to about 75% by weight of the system when using topically with 0.5 to 5 ml concentrations and preferably in 1 to 3 ml amounts.

The formulations of this invention are particularly useful in the administration of drugs that could be previously administered only by injection.

The transdermal delivery system described herein offers a major alternative especially for those individuals who have a history of undesirable side-effects associated with irritation and/or pain from the injection. Also for those patients who have already suffered damage, the transdermal preparations described herein present a new way of providing effective treatment and relief of painful symptoms.

Female sexual dysfunction is generally caused by vaginal dryness. Women most susceptible to vaginal dryness include menopausal women, women undergoing radiation therapy, and women suffering from an autoimmune disease. However, vaginal dryness is not limited to such women, and may be caused by numerous factors, many of which may be as yet unidentified. Because female sexual dysfunction has traditionally received significantly less attention than male sexual dysfunction, there is little literature available on the subject.

In many cases vaginal dryness is directly caused by vulvar dystrophy. The vulvar dystrophies are a common group of disorders in which various parts of the vulva atrophy or become dystrophic. While the vulvar dystrophies are common after menopause, they can occur at any time of life, even during childhood. Treatment is often unsatisfactory. See Horrobin, U.S. Pat. No. 5,380,757. Local hygiene and antipruritic ointments and creams may be beneficial but topical preparations containing either glucocorticoids or testosterone, the male sex hormone, are usually required. While these hormone based preparations are often effective, the glucocorticoids when used for long periods carry a serious risk of producing atrophy and thinning of the epithelium, while the testosterone preparations can produce clitoral enlargement or other masculinization.

Vaginal dryness can also be caused by pharmacological influences, for example, as a common side effect of many medications, including diuretics, antiarthritics and antidepressants. Generally, synthetic lubricants or synthetic moisturizers are prescribed for such situations, with limited effectiveness.

The methods and compositions of the present invention contemplate the treatment of female sexual dysfunction in its broadest manifestations. The drug delivery system which the present invention embodies is ideally suited for the topical application of formulations capable of containing an active agent and releasing said agent in a controlled manner to achieve efficacious transdermal drug delivery without the side effects which may accompany the same agent when used with delivery systems disclosed in the prior art. The formulations of the invention may be applied to the surface of the vagina, so that a therapeutically effective amount of the drug for treating vaginal dryness is released in a controlled manner, and thus the drug penetrates the exterior layers of the vagina to relieve said vaginal dryness.

In addition to the negative charged polymers, the transdermal polymer matrix must contain a non-ionic polymer which facilitates in retarding the absorption of the active drug through the skin and delays or slows down in animals natural absorption of the negatively charged polymer.

Without the presence of this component, the active drug would not be delivered transdermally into the site targeted for treatment at levels which are therapeutically effective. In addition to the non-ionic polymers described in this system, these materials are necessary to provide thorough penetration of skin layers including the epidermis, dermis and fatty tissue layers.

Particularly preferred nonionic polymers are cellulose derivatives and particularly those selected from the group consisting of carboxymethylcellulose sodium, hydroxyethyl cellulose, hydroxypropyl cellulose and mixtures thereof.

These particular polymers have been found to possess exceptional ability to form sustained release matrix formulations when used in combination with a negative charged polymer. Such polymers are generally employed in amounts of about 0.1% to about 1.5% and preferably about 0.5 to about 1.4%. Amounts above about 1.5% result in the formation of a solid gel when used with the negative charged polymer. Amounts below about 0.1% have not been found suitable to prepare a storage stable product that has sustained drug release.

A particularly preferred HEC concentration is about 0.2% to about 1.0% by weight of the matrix.

A wide variety of other medicaments which may be administered topically may be used in the delivery system according to this invention. These drugs include, without limitation, papaverine hydrochloride, phentolamine mesylate and prostaglandin $E_1$, nicotinic acid, glycerol, propylene glycol, testosterone, testosteronepropionate, glucocorticoids, hydrocortisone, gamma-linolenic acid (GLA), dihomo-gamma-linolenic acid (DGLA), Yerba Santa extract and mixtures thereof.

One particular criteria of the drug is that they must be solubilized in the polymer matrix solution in order to be topically administered.

The compositions and methods of the present invention are particularly helpful to invidiuals using a medication for preventing or treating hypertension (e.g., an antihypertensive medication) or heart disease, such as organic nitrates. While many currently available therapies for treating erectile dysfunction are contraindicated for individuals on such medications, the present invention is not so contraindicated. For example, oral admistration of sildenafil citrate (Viagra®, available from Pfizer) is contraindicated for individuals currently taking organic nitrates, such as nitroglycerine. See "VIAGRA® (sildenafil citrate) Tablets", Pfizer Labs, 7 (1998). Thus, the compositions and methods of the present invention may be used by individuals who are currently taking organic nitrates or other drugs which may be used to treat hypertension or heart disease. Moreover, with other currently available therapies which are not specifically contraindicated for use with antihypertensive medication, the dosing of the therapy must be carefully regulated to avoid adverse effects, thus typically preventing a therapeutically effective amount of drug from being delivered to the active site. Accordingly, there is a large group of individuals for whom the present invention may be the only safe and effective therapy.

As noted above, there are numerous causes of male erectile dysfunction. For example, it may be atonic, due to paralysis of the motor nerves without any evidence of lesions to the central nervous system, particularly the spinal cord. Alternatively, it could be psychic, and dependent on a mental problem or instability. Finally, it could be symptomatic, due to some other disorder, such as injury to nerves in the perineal region, by virtue of which the sensory portion of the erection reflex is blocked out. The compositions and methods of the present invention act independently of the particular cause.

Moreover, impotence may be of varying degrees. For example, impotence may be absolute, involving all sexual modalities; or total, affecting all sexual function, though not necessarily libido; or partial, affecting the rigidity or duration of the erection. Whether the cause of impotence is organic, due to structural changes, disease or some demonstrable functional impairment anywhere in the sexual system, psychogenic due to old age or sexual satiation, the result is the same; at least partial inability to engage in sexual activity due to the lack of an adequate erection. The compositions and methods of the present invention act independently of these varying degrees.

The following examples are illustrative of preferred embodiments of the invention and are not to be construed as limiting the invention thereto. All polymer molecular weights are average molecular weights. All percentages are based on the percent by weight of the final delivery system or formulation prepared unless otherwise indicated and all totals equal 100% by weight.

EXAMPLE 1

This example demonstrates the formation of a transdermal preparation of alprostadil.

The dosage range for the drug is between 2–3 ml.

| MATERIALS | |
|---|---|
| Alprostadil | 250 mcg |
| Sodium hyaluronate (NAHA) | 2.5% |
| Hydroxyethyl cellulose (HEC) | 0.7% |
| Methoxypolyethylene glycol (MPEG) | 10% |
| Benzyl alcohol | 1% |
| Water | Remainder |

Batch Size 1000 ml

1. Into a sterilized glass vessel is added 1062.5 ml of sterile water which is stirred at 1500 to 2000 rpm. Slowly add 34.5 grams of NAHA, having a molecular weight of around 700,000 to 775,000 and a purity described above. Allow to stir for 16 to 20 hours until all of the NAHA polymer has dissolved into the water and a crystal-clear viscous solution has formed.
2. Prepare a 0.7% solution of HEC by adding 10.5 grams of the solid material under aseptic conditions to 250 ml of sterile water. Allow to dissolve for 1 to 2 hours while stirring at 1500 to 2000 rpm. Add the HEC solution to a sufficient amount of the NAHA solution and mix for 10 to 15 hours until a homogeneous solution is produced.
3. Carefully measure 100 ml of methoxypolyethylene glycol (MPEG) 10% into the mixture. RPM speeds should be increased for the mixture while this step is being performed to 2500 rpm. The resulting mixture thus formed should be allowed to mix at 2000 rpm for an additional 3 to 4 hours.
4. At this point 1% of benzyl alcohol or 10 ml is added to the mixture. Again, the rpm speed is increased during this part of the procedure to 2500. The mixture should be allowed to mix for 3 to 5 hours at 2000 rpm.
5. Using safe techniques, 250 mg of alprostadil should be slowly added to the mixture. Again the rpm speed for the purpose of addition of drug should be increased to 2500, and the entire drug should be completed within 15 minutes.

The final mixture is clear with a slight tint following 15 to 20 hours of further mixing at 2000 rpm. The final product should be transferred, using aseptic techniques, to 1–5 ml tubes.

When used, approximately 2 ml of matrix is applied to the exterior surface of the penis 10 to 15 minutes before intercourse. Alternatively, approximately 2 ml may be infused into the urethra 10 to 15 minutes before intercourse. Either technique results in the formation of an erection.

EXAMPLE 2

A transdermal preparation of Alprostadil is prepared in the manner of Example 1 with the following components:

| | |
|---|---|
| Alprostadil | 0.15% |
| Sodium hyaluronate (NAHA) | 2.6% |
| Hydroxyethyl cellulose (HEC) | 0.3% |
| Methoxypolyethylene glycol (MPEG) | 5% |
| Benzyl alcohol | 1.5% |
| Water | Remainder |

The dosage range for the drug is between 2–3 ml.

EXAMPLE 3

A transdermal preparation of Alprostadil is prepared in the manner of Example 1 with the following components:

| | |
|---|---|
| Alprostadil | 0.3% |
| Sodium hyaluronate (NAHA) | 3.3% |
| Hydroxyethyl cellulose (HEC) | 0.5% |
| Methoxypolyethylene glycol (MPEG) | 10% |
| Benzyl alcohol | 2.5% |
| Water | Remainder |

The dosage range for the drug is between 2–3 ml.

EXAMPLE 4

A transdermal preparation of Alprostadil, prostaglandin-$E_1$-γ-cyclodextrin complex (a water-soluble source of prostaglandin $E_1$), formula is prepared in the following manner.

First, into a sterilized glass vessel is added 1062.5 ml of sterile water which is stirred at 1500 to 2000 rpm. To that solution, 34.5 grams of NAHA, having a molecular weight of around 700,000 to 775,000 and a purity described above, is slowly added. The resulting solution is then stirred for 16 to 20 hours until all of the NAHA polymer dissolves into the water and a crystal-clear viscous solution is formed.

Next, a 0.7% solution of HEC is prepared by adding 10.5 grams of the solid material under aseptic conditions to 250 ml of sterile water. The HEC solution is then allowed to dissolve for 1 to 2 hours while stirring at 1500 to 2000 rpm.

Then, the HEC solution is added to a sufficient amount of the NAHA solution and mixed for 10 to 15 hours until a homogeneous solution is produced. 100 ml of carefully measured methoxypolyethylene glycol (MPEG) 10% is added into the mixture. The stirring speed should be increased for the mixture, while this step is being performed, to 2500 rpm. The resulting mixture thus formed should be allowed to mix at 2000 rpm for an additional 3 to 4 hours. Next, 10 ml of benzyl alcohol (1%) is added to the mixture. Again, the stirring speed is increased during this part of the procedure to 2500 rpm. Then, the mixture is stirred for 3 to 5 hours at 2000 rpm.

Finally, to 6.6 ml of the NAHA/HEC polymer matrix thus formed, 20 mg of powdered Alprostadil (prostaglandin-$E_1$-γ-cyclodextrin) complex is added. The resulting mixture is then mixed by hand for thirty minutes so as to insure that the Alprostadil is in solution, and that the gel is clear. This mixture is then refrigerated to allow air bubbles to come to the surface and dissipate. 1 ml of the gel thus formed is then charged into 3 ml syringes giving 1200 mcg of Alprostadil per dose.

EXAMPLE 5

A transdermal preparation of Alprostadil (prostaglandin $E_1$) formula was prepared in the following manner.

First, 20 ml of prostaglandin $E_1$ was dissolved in 1.5 ml of propylene glycol. The resulting solution was mixed by hand until the prostaglandin $E_1$ appears to be totally dissolved. Next, 5 ml of an NAHA/HEC polymer gel, prepared as described in Example 4, was added to the solution. The substance was then mixed by an electric stirrer for 2 hours. A 0.5 ml sample was removed from the resulting mixture. Slight separation in the mixture was observed. An additional 1 ml of propylene glycol was added to the mixture followed by mixing for an additional hour. The resulting mixture is observed to be very opaque.

EXAMPLE 6

A transdermal preparation of Alprostadil (0.4%) formula is prepared in the following manner.

First, a mixture is prepared by dissolving 14.7 grams of Sodium Hyaluronate (NAHA) in 350 ml of water, then stirring the resulting solution at 1800 rpm initially, reducing to 800 rpm and stirring for 2 hours, and then stirring at a low speed overnight. To the resulting mixture is added a mixture of 75 ml MPEG, and then 12.5 ml of benzyl alcohol, stirred for 30 minutes, is added. The resulting mixture is then stirred for 2 hours.

Next, a solution is prepared by adding 3.5 g (0.7)% HEC to 75 ml of water and stirring for 35 minutes. The resulting solution is then added to the above formed mixture and stirred at a moderate speed overnight to form an NAHA/HEC polymer matrix.

Then, 40 mg of prostaglandin $E_1$ is added to 10 ml of the NAHA/HEC polymer matrix. The mixture is stirred for 2 hours. 0.5 to 0.75 ml of the resulting gel is loaded into syringes and stored in a refrigerator.

EXAMPLE 7

A topical gel formula for treating vaginal dryness is prepared in the manner of Example 6 by using a mixture of nicotinic acid and glycerol in place of prostaglandin $E_1$.

EXAMPLE 8

A topical gel formula for treating vaginal dryness is prepared in the manner of Example 6 by using a steroid, such as testosterone, in place of prostaglandin $E_1$.

EXAMPLE 9

A transdermal preparation of Alprostadil (0.4%) formula (Batch Size 1000 ml) is prepared in the following manner.

First, a mixture is prepared by dissolving 24 grams of (2.4%) Sodium Hyaluronate (NAHA) in 710 ml of water, mixing at a high speed for two hours or until clear, then reducing speed to 200–500 rpm and continuing to stir for 24 hours.

Next, a solution is prepared by adding 5 grams HEC powder to 200 ml of water and stirring at a high speed (2000–2500 rpm) for 35 minutes. The resulting solution is then added to the above formed mixture and mixed for 24 hours.

Then, 5 grams Niacin (5%) is added to the above mixture and mixed for 24 hours. The resulting gel is loaded into 30 ml glass jars with Teflon lined caps.

EXAMPLE 10

A transdermal preparation of Alprostadil and Niacin formula (Batch Size 1000 ml) is prepared in the following manner.

First, a mixture is prepared by dissolving 24 grams of (2.4%) Sodium Hyaluronate (NAHA) in 710 ml of water, mixing the resulting solution at 2000 rpm for two hours or until clear, then reducing speed to 200–500 rpm and continuing mixing for 24 hours.

Next, a solution is prepared by adding 5 grams HEC powder to 200 ml of water and stirring for 35 minutes. The resulting solution is added to the above formed mixture and mixed for 24 hours. To this solution, 5 grams of Niacin (5%) is added and mixed for 24 hours.

Then, 80 ml MPEG is slowly added to 1 gram of Alprostadil and mixed at a speed of 600 rpm until fully dissolved but at least for 5 hours, reducing speed to 300 rpm and continuing mixing for 12 hours.

Finally, using aseptic technique, suitable applicators are filled with 2.4 ml of the completed matrix. The final dosage form is stored in a refrigerator at 0–3 degrees Celcius.

EXAMPLE 11

A transdermal preparation of Alprostadil (Prostaglandin $E_1$) formula is prepared in the following manner.

First, a mixture is prepared by dissolving 24 grams of (2.4%) Sodium Hyaluronate (NAHA) in 710 ml, mixing the resulting solution at 2000 rpm for 2 hours or until clear, then reducing speed to 200–500 rpm and continuing mixing for 24 hours.

Next, a solution is prepared by adding 5 grams of HEC powder to 200 ml water, mixing at 2000–2500 rpm for 35 minutes. The resulting solution is then added to the above formed mixture and mixed for 24 hours.

Then, a solution is prepared by slowly adding 1 gram of Alprostadil (Prostaglandin $E_1$) to 80 ml MPEG and mixing at 600 rpm until fully dissolved but at least for 5 hours, then mixing at 300 rpm for 12 hours.

Finally, using aseptic technique, suitable applicators are filled with 2.4 ml of the completed matrix. The final dosage form is stored in a refrigerator at 0–3 degrees Celcius.

The invention being thus described, it will be obvious that the same may be varied in many ways. Such variations are not to be regarded as a departure from the spirit and scope of the invention and all such modifications are intended to be included within the scope of the following claims.

We claim:

1. A gelled composition for treating sexual dysfunction in an animal, which comprises: a therapeutically effective amount of a drug which causes vasodilation dispersed within a matrix comprising hyaluronic acid or derivatives thereof blended with a nonionic polymer; wherein the molar ratio of the hyaluronic acid or derivatives thereof to the nonionic polymer is 1:4 to 0.09; and wherein the hyaluronic acid or derivatives thereof is present in amounts of about 1.0% to about 3.5% by weight.

2. The gelled composition of claim 1, wherein the hyaluronic acid or salts thereof is the sodium salt and has a sulphonated ash content below about 15%, a protein content below about 5% and a purity of at least 98%.

3. The gelled composition of claim 1, wherein the hydroxyethyl cellulose has a viscosity of about 1,500 cps for a 5% solution to about 5,500 cps for a 1% solution.

4. The gelled compostion of claim 1, wherein the drug which causes vasodilation is selected from the group consisting of nitrovasodilators, ACE inhibitors, angiotensin receptor antagonists, phosphodiesterase inhibitors, direct vasodilators, adrenergic receptor antagonists, calcium channel blocking drugs, alpha blockers, beta blockers, lympathomimetics, vitamins, organic nitrates and mixtures thereof.

5. The gelled compostion of claim 1, wherein the drug which causes vasodilation is selected from the group consisting of niacin, nitroglycerine, nilatrin hydrochloride, pentoxyphylene, phenoxybenzamine, dichlophenac, papaverine, hydralzaine, sodium nitroprusside, isoxaprine hydrochloride, nylidrin hydrochloride, tolazoline hydrochloride, nicotinyl alcohol, phentolamine and mixtures thereof.

6. The gelled composition of claim 1, wherein the drug which causes vasodilation is selected from the group consisting of niacin, nicotinic acid, nicotinic acid precursors, esters of nicotinic acid and mixtures thereof.

7. The gelled composition of claim 6, wherein the niacin, nicotinic acid, nicotinic acid precursors, esters of nicotinic acid or mixtures thereof is present in amounts of about 1% to about 15% by weight.

8. The gelled composition of claim 1, wherein the therapeutically effective amount of the drug is from about 1 ml to about 3 ml.

9. The gelled composition of claim 1, wherein the animal is using a medication for preventing or treating hypertension or heart disease.

10. The gelled composition of claim 1, wherein the animal is currently taking an antihypertensive medication.

11. The gelled composition of claim 1, wherein the polymer matrix is storage stable.

12. The gelled composition of claim 1, wherein the hydroxyethyl cellulose is present in amounts of about 0.1% to about 1.5% by weight.

* * * * *

UNITED STATES PATENT AND TRADEMARK OFFICE
CERTIFICATE OF CORRECTION

PATENT NO.    : 6,251,436 B1
DATED         : June 26, 2001
INVENTOR(S)   : Alan Drizen et al.

It is certified that error appears in the above-identified patent and that said Letters Patent is hereby corrected as shown below:

Column 17,
Line 49, after "hyaluronic acid or" and before "thereof", please replace "derivatives" with -- salts --.
Line 50, after "blended with" and before ";", please replace "a nonionic polymer" with -- hydroxyethyl cellulose --.

Column 18,
Lines 1 through 2, after "hyaluronic acid or" and before "thereof", please replace "deriva-tives" with -- salts --.
Line 2, after "thereof to the" and before "is 1:4 to 0.09", please replace "nonionic polymer" with -- hydroxyethyl cellulose --.
Line 3, after "hyaluronic acid or" and before "thereof", please replace "derivatives" with -- salts --.

Signed and Sealed this

Twenty-eighth Day of January, 2003

JAMES E. ROGAN
*Director of the United States Patent and Trademark Office*